US012746141B2

(12) United States Patent
Hammond, III et al.

(10) Patent No.: US 12,746,141 B2
(45) Date of Patent: Sep. 29, 2026

(54) HALO INTRINSIC TRACTION (HIT) DEVICE FOR PREOPERATIVE CURVATURE CORRECTION OF SEVERE PEDIATRIC SCOLIOSIS AND/OR KYPHOSIS

(71) Applicants: Georgia Tech Research Corporation, Atlanta, GA (US); Children's Healthcare of Atlanta, Inc., Atlanta, GA (US)

(72) Inventors: Frank L. Hammond, III, Atlanta, GA (US); Charles Brenner, Atlanta, GA (US); Brian Emling, Atlanta, GA (US); Kinsey Herrin, Atlanta, GA (US); Scott J. Hollister, Atlanta, GA (US); Uzma Mhate, Atlanta, GA (US); Michael Schmitz, Atlanta, GA (US); Richard Welling, Atlanta, GA (US)

(73) Assignees: GEORGIA TECH RESEARCH CORPORATION, Atlanta, GA (US); CHILDREN'S HEALTHCARE OF ATLANTA, Atlanta, GA (US)

( * ) Notice: Subject to any disclaimer, the term of this patent is extended or adjusted under 35 U.S.C. 154(b) by 90 days.

(21) Appl. No.: 18/637,953

(22) Filed: Apr. 17, 2024

(65) Prior Publication Data

US 2024/0341992 A1 Oct. 17, 2024

Related U.S. Application Data

(60) Provisional application No. 63/496,648, filed on Apr. 17, 2023.

(51) Int. Cl.
*A61F 5/048* (2006.01)
*A61F 5/058* (2006.01)

(52) U.S. Cl.
CPC .......... *A61F 5/048* (2013.01); *A61F 5/05883* (2013.01)

(58) Field of Classification Search
CPC ... A61N 1/3604; A61F 5/048; A61F 5/05883; A61F 5/0123; A61F 5/013; A61F 5/37;

(Continued)

(56) References Cited

U.S. PATENT DOCUMENTS 3,669,102 A * 6/1972 Harris .................... A61F 5/055 602/40
4,620,530 A 11/1986 Lanier et al.

(Continued)

OTHER PUBLICATIONS

Bouchoucha, S. et al., "Progressive correction of severe spinal deformities with halo-gravity traction," Acta Orthopaedica Belgica, 77(4). (6 Pages).

(Continued)

*Primary Examiner* — Alireza Nia
*Assistant Examiner* — Michael Milo
(74) *Attorney, Agent, or Firm* — TROUTMAN PEPPER LOCKE LLP; Ryan A. Schneider; Stephanie J. Remy

(57) ABSTRACT

A halo intrinsic traction (HIT) system including a first support, a second support, and a first actuator. The first support can be configured to attach to a head portion of a patient. The second support can be configured to attach to a (Continued)

body portion of a patient, the body portion being below the head portion. The first actuator can be configured to generate an expansion force between the first and second supports. The halo intrinsic traction device builds upon the proven principles of halo-gravity traction, and can induce constant and controlled traction across the spine while in a smaller, wearable form factor.

18 Claims, 8 Drawing Sheets

(58) Field of Classification Search
CPC .. A61F 5/30; A61F 5/01; A61F 5/0109; A61F 2005/0155; A61F 2005/0167; A61F 2005/0179; A61F 2005/0181; A61H 1/02; A61H 1/0237; A61H 1/0262; A61H 2003/007; A61H 2201/1645; A61H 2201/1652; B25J 9/0006; A41D 13/1254; A41D 13/0543; A43B 71/1125
USPC ............................................................ 602/36
See application file for complete search history.

(56) References Cited

U.S. PATENT DOCUMENTS

| | | | | | |
|---|---|---|---|---|---|
| 4,632,099 | A * | 12/1986 | Mollo | A61F 5/055 | 602/18 |
| 4,765,317 | A * | 8/1988 | Eastman | A61F 5/055 | 602/32 |
| 5,063,920 | A * | 11/1991 | Moore | A61F 5/055 | 602/18 |
| 5,195,947 | A * | 3/1993 | Bode | A61F 5/055 | 602/17 |
| 6,659,972 | B2 | 12/2003 | Stemper | | |
| 2002/0151831 | A1* | 10/2002 | Stamper | A61F 5/055 | 602/5 |
| 2009/0171469 | A1* | 7/2009 | Thorsteinsson | A61B 5/4585 | 623/26 |

OTHER PUBLICATIONS

Sink, E. L. et al., "Efficacy of perioperative halo-gravity traction in the treatment of severe scoliosis in children," (2001). Journal of Pediatric Orthopaedics, 21(4). https://doi.org/10.1097/00004694-200107000-00020. (6 Pages).

* cited by examiner

HALO INTRINSIC TRACTION (HIT) DEVICE FOR PREOPERATIVE CURVATURE CORRECTION OF SEVERE PEDIATRIC SCOLIOSIS AND/OR KYPHOSIS

CROSS-REFERENCE TO RELATED APPLICATIONS

This application claims the benefit of U.S. Provisional Application Ser. No. 63/496,648, filed on 17 Apr. 2023, which is incorporated herein by reference in its entirety as if fully set forth below.

FIELD OF THE DISCLOSURE

The various embodiments of the present disclosure relate generally to systems and methods for treating spinal curvature defects.

BACKGROUND

Scoliosis is the lateral curvature of the spine such that it deviates from the otherwise straight and anatomically typical position. The prevalence of scoliosis has been widely reported as low as 1-3% to as high as 15% of the population. Of the patient population, approximately 2-3 of every 1,000 people will require treatment for progressive scoliosis. Unlike a healthy spine, a scoliotic spine, seen in FIG. 2D, can have a lateral convex curvature accompanied by a rotational element as well. Scoliosis is primarily diagnosed by a spinal curvature of 10° or more in the coronal plane measured on a standing anteroposterior X-ray image; this measure of curvature is referred to as the cobb angle. Radiographically, the cobb angle is measured by drawing a line along the inferior edge of the uppermost end vertebra and the superior edge of the inferior most end vertebra. The cobb angle can be a measure of scoliosis severity; an example of a cobb angle measurement is depicted in FIG. 2B. The end vertebrae are the two vertebrae whose end plates are most tilted with respect to one another. In addition, the cobb angle can capture multiple curvatures in one measurement. Even though scoliosis is well-defined and can be easily diagnosed, the etiology behind scoliosis can be more difficult to decipher.

Scoliosis can arise out of vertebral malformations, neuromuscular disorders, or syndromic disorders. Idiopathic scoliosis, of infantile, pediatric, adolescent, or adult, is a diagnosis of exclusion when other causes have been ruled out. In other words, if an external condition cannot be determined as the cause of a patient's scoliosis, its origin is simply unknown. This leaves a gap in the scientific understanding of scoliosis as well as the methods to effectively treat the condition.

Like scoliosis, kyphosis is also an abnormality in the curvature of the spine. Specifically, kyphosis is the abnormal curvature of the spine in the sagittal plane, with a posterior convexity. A healthy spine, as seen in FIG. 2A has a smooth curvature in the sagittal plane with an inward curve in the cervical region, an outward curve in the thoracic region, followed by an inward curve in the lumbar region, and lastly an outward curvature in the sacral region. Kyphosis violates this pattern with either a sharp angle, known as angular kyphosis or a gradual curve, known as round kyphosis. Angular kyphosis is the more severe of the two conditions and universally requires treatment. Round kyphosis, shown in FIG. 2C, is more tolerable and is the cause behind the condition colloquially referred to as "hunch back." Scoliosis and kyphosis can occur independently of one another, but both conditions can be present in severe cases: kyphoscoliosis.

Current Clinical Treatment and Practice

Scoliosis, kyphosis, and other related spinal deformities are often treated using an external orthosis, commonly referred to as a TLSO (thoracic-lumbar-sacral orthosis) or brace, which applies both normal and rotational forces to stabilize the spine and prevent it from deforming further over time. Braces are typically prescribed when spinal curve is likely to progress. The efficacy of braces to reduce the need for corrective surgery is well established, and orthoses are still the best nonoperative means to prevent condition progression.

A scoliosis or kyphosis brace typically covers the patient's torso, spanning from the underarms to the pelvis, and is custom fit to each patient to keep the spine straight and apply optimal corrective forces. To create a brace, an orthotist chooses from a variety of different polymer materials, such as polypropylene and copolymers, depending on the design best suited for the patient's needs, and vacuum forms the polymer structure to a model of the patient's anatomy to ensure a tight, comfortable fit and promote patient compliance. The orthotist will also shape the upper and lower trims of the brace and add personalized features such as accessory attachment points and feeding tube openings if necessary.

Boston TLSOs typically include a one-or two-part brace custom formed to a model of the patient to provide preventative forces on the convex region of the curve, with corresponding cutouts on the concave region of the curve. The aligned regions of high and low pressure are intended to push the patient's spine laterally into the proper position. They are lined with plastaezote foam for comfort, compliance, and pressure injury reduction. TLSOs have a typical prescription of 18-23 hours per day for 6-18 months but this varies case-to-case. However, bracing is not always an appropriate treatment for all patients. Dependent on the presentation of the curve and current or anticipated impacts on lung and heart function, surgery may be necessary as a first course treatment. Of the patient population that needs treatment for scoliosis, 1 of every 1,000 patients will require surgery. Surgical intervention is typically pursued if the patient's cobb angle is severe (greater than 45°) and impacts cardiac and pulmonary function. Primarily, patients are treated with a series of rods and pins and or vertebral fusion to maintain the desired position. This consists of pedicle screws inserted into two or more vertebrae, with a stiff rod spanning the vertebrae and connecting the screws. Vertebral fusion involves the fusion of the curved vertebra in an aligned position into effectively a singular bony structure.

Operative treatment is not without its drawbacks as there has been a varying but high rate of complications reported. On average, idiopathic scoliosis cases have a 20% complication rate of some kind, which includes pseudarthrosis, neurological complications, and pedicle screw misplacements. These risks incur on top of the risks associated with all major surgeries such as blood loss and infections. In addition, the overall financial cost can be burdensome for families. Risks are inherent for a procedure of this magnitude, but overall, the operation is considered very safe, with a fatality rate of less than 1%. These risks of complications further emphasize the need for effective nonoperative and preoperative correction methods.

Current Preoperative Correction Methods

Preoperative correction is necessary for severe scoliosis and kyphosis cases as it reduces the risk of damage to nervous and other soft tissues in the spine, strengthens Musculo-skeletal tissues supporting the spine, reduces recovery time, and is responsible for up to half of the curvature correction gained from the procedure. Preoperative traction is achieved by putting the spine under mechanical tension and implemented until operative readiness-determined as the correction of approximately half of the patient's original curvature or an increase in pulmonary function.

Halo gravity traction (HGT) is the most common form of preoperative traction and utilizes a halo, a system of weights, pullies, and gantry. For HGT, patients are fitted with a halo ring secured with 4-8 pins around the skull's equator. The halo is directly supported by the TLSO through four rigidly attached vertical uprights, which are connected to the halo via two horizontal rails. An example of this, seen in FIG. 3, is manufactured by PMT© Corporation and stabilizes a patient's entire spine. The effectiveness of HGT has been thoroughly proven, with an average improvement of 15-25°. HGT is primarily an inpatient intervention that takes advantage of the constant forces of gravity to induce traction essentially 24 hours a day, 7 days a week. HGT traction starting weight is 10% of the patient's body weight, increased incrementally over the treatment time, without exceeding 50% of the patient's body weight. HGT treatment duration depends on the severity of the patient's condition, rate of correction, and the logistical and financial constraints of the patient and the hospital, but usually spans 4-8 weeks with most of the correction occurring in the first 2 weeks. The magnitude of traction is reduced at night to reduce superior movement while lying supine during sleep. Due to the bulky equipment required for HGT, as seen in FIG. 3, patients are limited to hospital rooms, beds, walkers, and wheelchairs that are fitted with the HGT gantry system, drastically reducing their quality of the life.

BRIEF SUMMARY

An exemplary embodiment of the present disclosure provides a halo intrinsic traction (HIT) system, comprising a first support, a second support, and a first actuator. The first support can be configured to attach to a head portion of a patient. The second support can be configured to attach to a body portion of a patient, the body portion being below the head portion. The first actuator can be configured to generate an expansion force between the first and second supports.

In any of the embodiments disclosed herein, the first actuator can comprise a spring configured to generate the expansion force.

In any of the embodiments disclosed herein, the first actuator can comprise a first end coupled to the first support and a second end coupled to the second support, and the spring can apply a force pushing the first end away from the second end.

In any of the embodiments disclosed herein, the first actuator can comprise an adjustment actuator configured to adjust a magnitude of the force between the first and second supports.

In any of the embodiments disclosed herein, the adjustment actuator can be moveable between a plurality of positions, and each position can correspond to a different magnitude of the force between the first and second supports.

In any of the embodiments disclosed herein, the first actuator can comprise an anti-tampering lock configured to transition between a locked and an unlocked position, and the adjustment actuator can be moveable between the plurality of positions only when the anti-tampering lock is in the unlocked position.

In any of the embodiments disclosed herein, each of the plurality of positions can correspond to a predetermined fixed incremental change in the magnitude of the force between the first and second supports.

In any of the embodiments disclosed herein, the first actuator can be interchangeable with one or more other actuators, and the first actuator and the one or more other actuators can be configured to generate differing expansion forces.

In any of the embodiments disclosed herein, the first support can comprise a halo member configured to attach to the head portion of the patient.

In any of the embodiments disclosed herein, the halo member can be coupled to the first actuator via a rotatable coupler, such that rotation of the coupler can alter a direction of the expansion force applied to the first support relative to the second support.

In any of the embodiments disclosed herein, the first actuator can be coupled to a first side of the halo member, and the system can further comprise a second actuator coupled to a second side of the halo member and configured to generate an expansion force between the first and second supports.

Another embodiment of the present disclosure provides a method of treating scoliosis in a patient in need thereof. The method can comprise: attaching a first support to a head portion of a patient; attaching a second support to a body portion of the patient, the body portion being below the head portion; generating, with an actuator, an expansion force between the first and second supports (which can result in spinal distraction).

In any of the embodiments disclosed herein, the first support can comprise a halo member, and wherein the step of attaching a first support to the head portion of a patient can comprise attaching the halo member to the head portion of the patient.

These and other aspects of the present disclosure are described in the Detailed Description below and the accompanying drawings. Other aspects and features of embodiments will become apparent to those of ordinary skill in the art upon reviewing the following description of specific, exemplary embodiments in concert with the drawings. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments discussed herein. In similar fashion, while exemplary embodiments may be discussed below as device, system, or method embodiments, it is to be understood that such exemplary embodiments can be implemented in various devices, systems, and methods of the present disclosure.

BRIEF DESCRIPTION OF THE DRAWINGS

The following detailed description of specific embodiments of the disclosure will be better understood when read in conjunction with the appended drawings. For the purpose of illustrating the disclosure, specific embodiments are shown in the drawings. It should be understood, however, that the disclosure is not limited to the precise arrangements and instrumentalities of the embodiments shown in the drawings.

DETAILED DESCRIPTION

To facilitate an understanding of the principles and features of the present disclosure, various illustrative embodiments are explained below. The components, steps, and materials described hereinafter as making up various elements of the embodiments disclosed herein are intended to be illustrative and not restrictive. Many suitable components, steps, and materials that would perform the same or similar functions as the components, steps, and materials described herein are intended to be embraced within the scope of the disclosure. Such other components, steps, and materials not described herein can include, but are not limited to, similar components or steps that are developed after development of the embodiments disclosed herein.

Figures 1A, 1B:
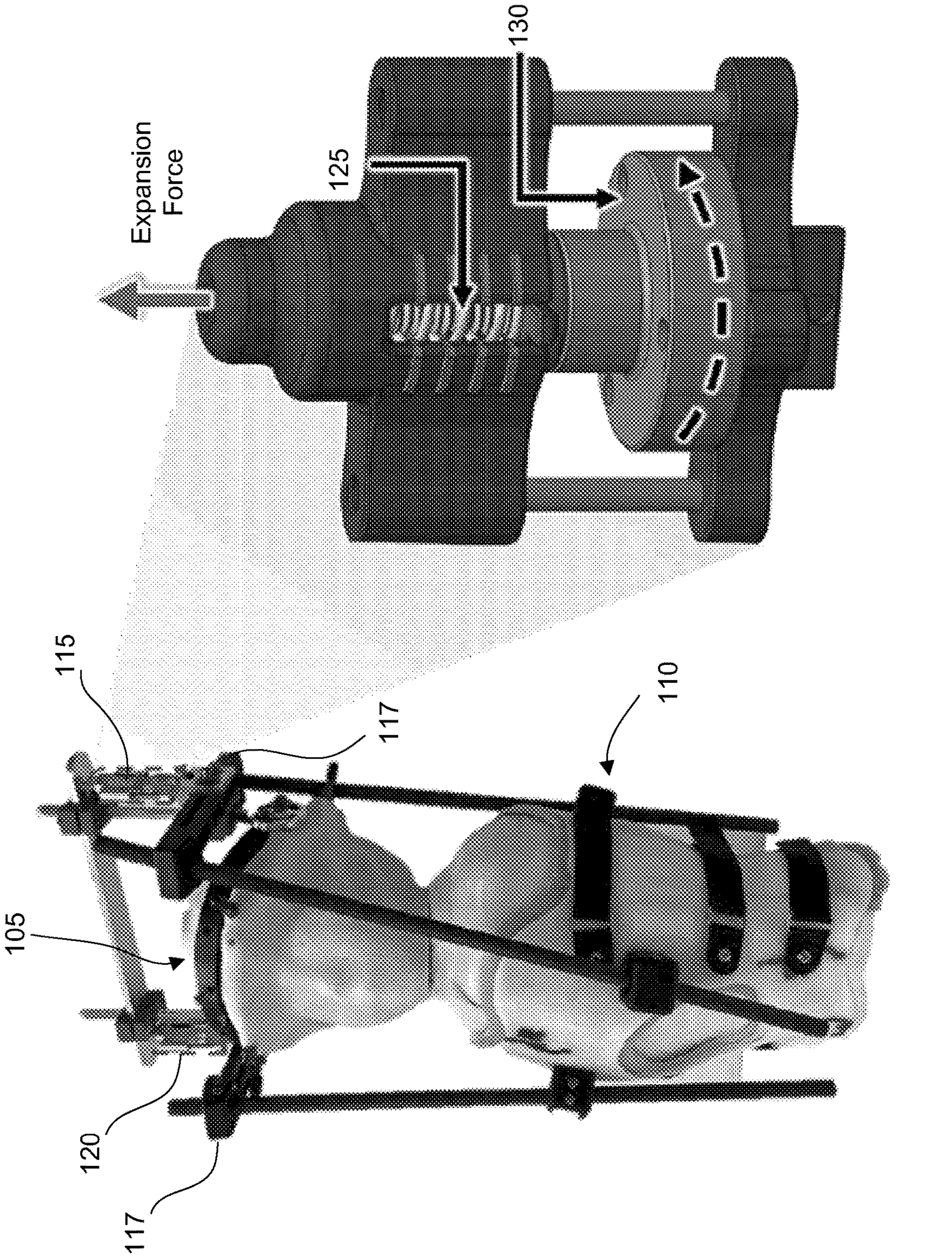
FIG. 1A provides an exemplary embodiment of a halo intrinsic traction (HIT) system, and FIG. 1B provides an exemplary embodiment of an actuator, in accordance with some embodiments of the present disclosure.
Figure 2A:
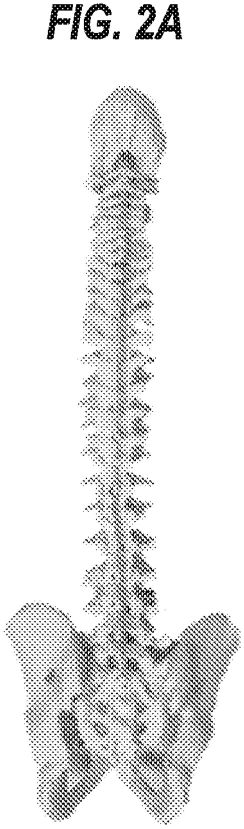
FIGS. 2A-D provide depictions of a healthy spine (FIG. 2A), a spine with scoliosis showing measurement of cobb angle (FIG. 2B), a spine with kyphosis (FIG. 2C), and a spine with scoliosis (FIG. 2D).
Figure 2B:
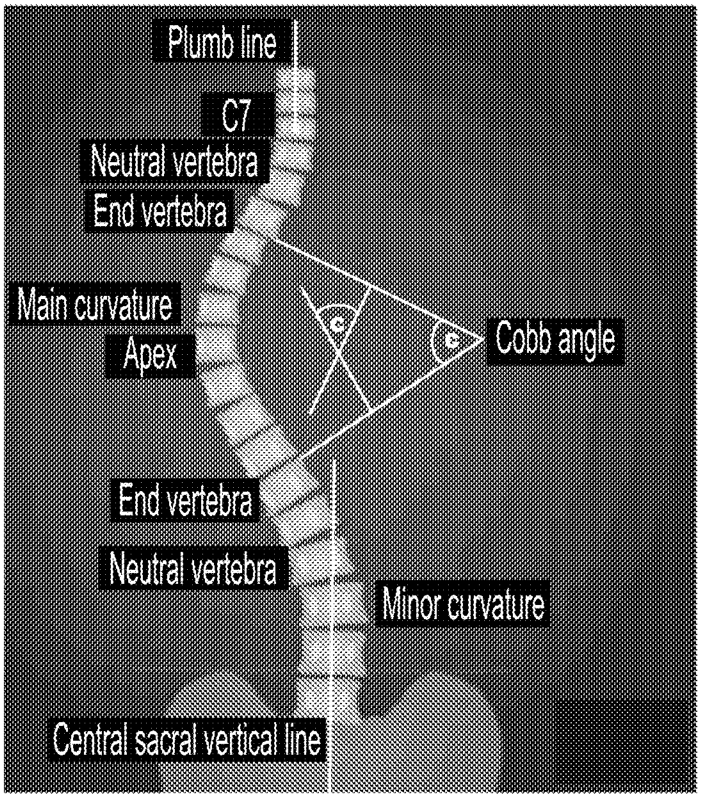
Figure 2C:
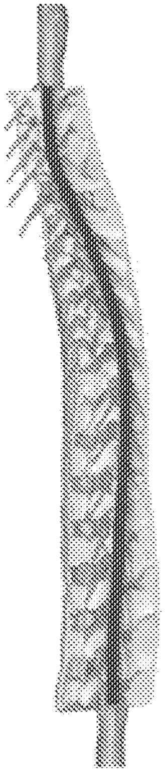
Figure 2D:
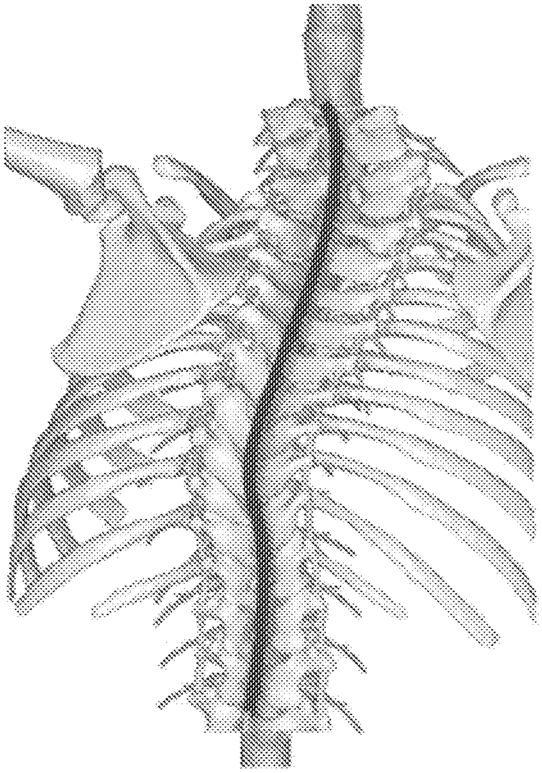
Figure 3:
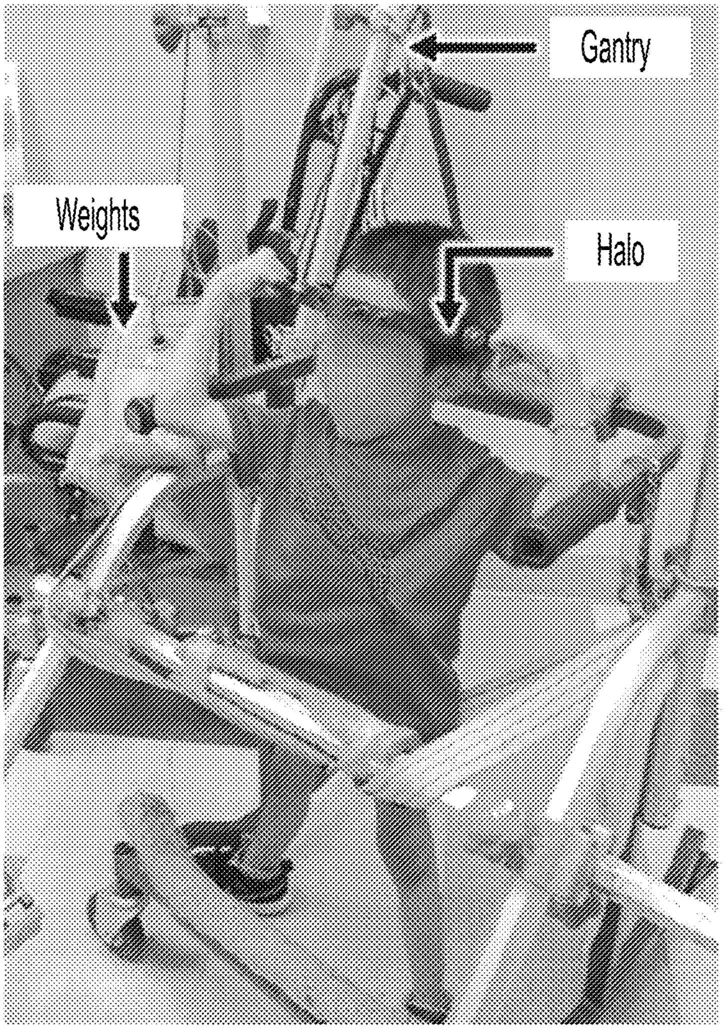
FIG. 3 (Prior Art)
FIG. 3 provides a photograph of a subject utilizing a conventional halo gravity traction (HGT) system.

As a result of the lack of modernized treatments available, some embodiments of the present disclosure provide a Halo Intrinsic Traction device, or HIT device. The HIT device builds upon the proven principles of HGT, and can induce constant and controlled traction across the spine while implementing them in a smaller, wearable form factor, as seen in FIG. 1A. Contrary to conventional HGTs, the HIT devices disclosed herein can use an actuator configured to deliver an expansion force (e.g., an internal compression spring), rather than gravity, to induce traction along the patient's spine (spinal distraction). For example, a spring can sit between top and bottom housing of the actuator, such that the entire device is compressible. The intended use of some of the HIT devices disclosed herein can mirror the clinical use and patient population of HGT. As such, the HIT device can be used for preoperative curvature correction for pediatric scoliosis and or kyphosis patients who are already fitted with or qualify for a halo ring. In some embodiments, the actuators can be used in parallel with one on each side of the patient's halo. They can be mounted via customized hardware that interfaces seamlessly with currently available medical devices.

As shown in FIG. 1A, an exemplary embodiment of the present disclosure provides a halo intrinsic traction (HIT) system, comprising a first support 105, a second support 110, and a first actuator 115. The first support 105 can be any support structure or combination of structures configured to attach to a head portion of a patient. For example, as discussed below, as shown in FIG. 1A, in some embodiments, the first support 105 can comprise a halo member. The second support be any support structure or combination of structures configured to attach to a body portion of a patient, the body portion being below the head portion. The first actuator 115 can be configured to generate an expansion force between the first 105 and second 110 supports. The expansion force from the first actuator 115 can apply a traction force between the first support (head portion of the subject) and second support (body portion of the subject).

Figure 4A:
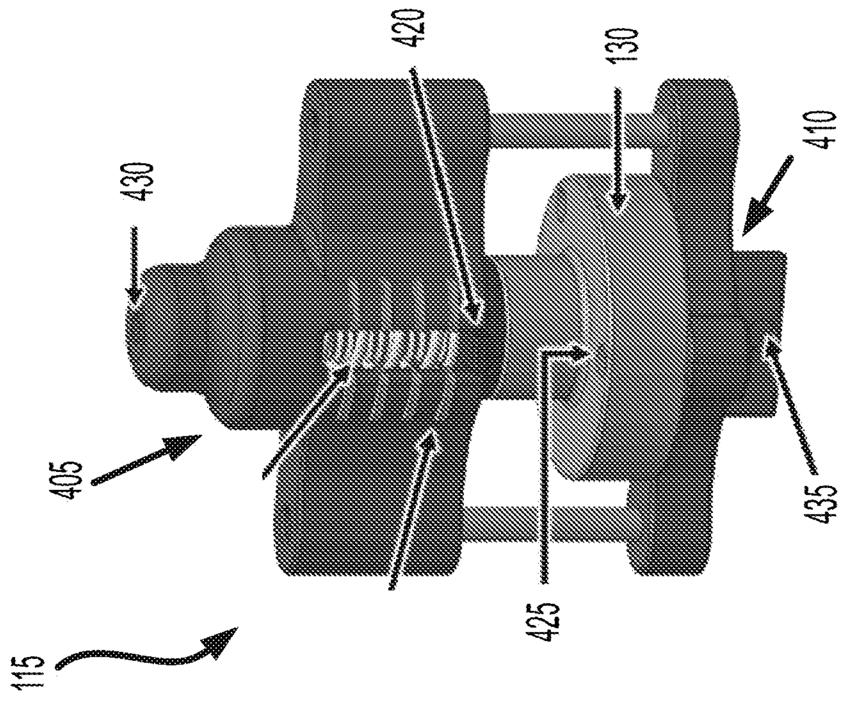
FIGS. 4A provide schematics of components of a HIT system, in accordance with some embodiments of the present disclosure.

The first actuator can be many different actuators configured to generate an expansion force. For example, as shown in FIGS. 1B and 4A, in some embodiments, the first actuator 115 can comprise a spring 125 configured to generate the expansion force. The disclosure, however, is not limited to spring actuators. Rather, other embodiments can employ actuators that generate an expansion force by other means, including, but not limited to, inflatable balloons, hydraulics, expandable polymers (or other expandable materials), and the like.

As shown in FIG. 4A, in some embodiments, the first actuator can comprise a first end 405 coupled to the first support and a second end 410 coupled to the second support, and the spring can apply an expansion force pushing the first end away from the second end. For example, the first end 405 can comprise an upper positioning bore configured to attach to the first support 105 Similarly, the second end 410 can comprise a lower positioning bore 435 configured to attach to a portion of the second support 110.

As shown in FIGS. 1B & 4A, in some embodiments, the first actuator 115 can comprise an adjustment actuator 130 configured to adjust a magnitude of the force between the first and second supports. The adjustment actuator 130 can be any actuator for adjusting the magnitude of the expansion force generated by the first actuator 115. For example, as shown in FIG. 4A, in some embodiments, the adjustment actuator 130 can be moveable (e.g., rotatable) between a plurality of positions, and each position can correspond to a different magnitude of the expansion force between the first and second supports. In some embodiments, each of the plurality of positions can correspond to a predetermined fixed incremental change in the magnitude of the expansion force between the first and second supports. The actuator 115 can also comprise a scale indicator 420 to indicate the current selected value for the expansion force. Thus, by rotating the adjustment actuator 130, the magnitude of the expansion force can be altered to a predetermined value.

In some embodiments, the first actuator can comprise an anti-tampering lock 425 configured to transition between a locked and an unlocked position, such that the adjustment actuator 130 can be moveable between the plurality of positions only when the anti-tampering lock is in the unlocked position. The anti-tampering lock 425 can be many different locks. For example, in some embodiments, as shown in FIG. 4A, the anti-tampering lock can comprise one or more bore holes. One or more of the bore holes can be engaged (e.g., via a pin inserted therein) to prevent adjustment of the adjustment actuator 130.

In some embodiments, the first actuator 115 can be interchangeable with one or more other actuators, and the first actuator 115 and the one or more other actuators can be configured to generate differing expansion forces. For example, the first actuator 115 may be configured to be adjustable between a first range of expansion forces, while the one or more other actuators can be configured to be adjustable through one or more other ranges of expansion forces. Thus, depending on the expansion force desired for a particular subject, an appropriate interchangeable actuator can be selected.

Figure 4B:
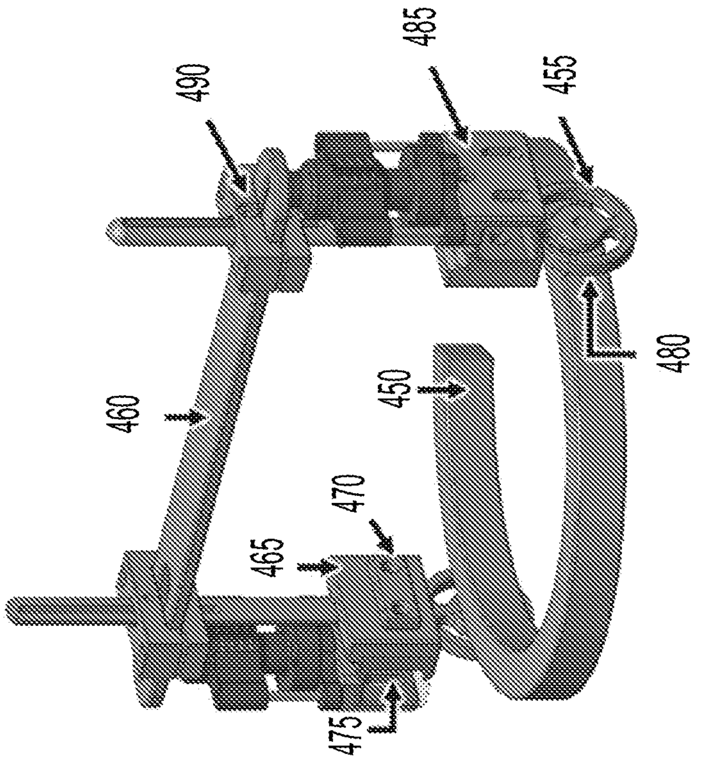
FIG. 4B provides a schematic of some components of a HIT system, in accordance with some embodiments of the present disclosure.

As shown in FIG. 4B, in some embodiments, the first support 105 can comprise a halo member 450 configured to attach to the head portion of the patient. The halo member 450 can be many halo members known in the art. In some embodiments, the halo member 450 can be attached to a head portion of the subject via screws and/or pins.

In some embodiments, the halo member can be coupled to the first actuator via a rotatable coupler 455, such that rotation of the coupler 455 can alter a direction of the expansion force applied to the first support relative to the second support. Accordingly, in some embodiments, the HIT system allows clinicians to adjust the ML angle of the traction profile which was not possible in conventional systems.

As shown in FIG. 4B, in some embodiments, the HIT system can comprise other components for positioning the HIT system (e.g., first support 115) appropriately, including, but not limited to, an overhead bar 460, and anterior-posterior positioner block 465, anterior-posterior positioner hardware 470, a rail interface 475, a halo interface 480, a bottom mount 485, and/or a medial-lateral positioner block 490. These components can secure the anterior-posterior (AP), medial-lateral (ML), and superior-inferior (SI) positions of the devices and allow for the force of the HIT devices to be translated to the patient's spine. These components can be designed with adjustable positioning so the HIT devices can be positioned according to the attending clinician's discretion. Once aligned, the AP and ML position of the HIT device can be secured with the hardware and set screws incorporated into the mounting components. The AP positioning system 465 470 and bottom mount 485 for the HIT device can interface via the rail interface 475 with the horizontal rails 117 shown in FIG. 1A. The force output from the actuator 115 can be transferred to the halo member 450 via the overhead bar 460 and the rotatable coupler 455. The rotatable coupler 455 can mount to the halo member 450 and have the ability to rotate about the frontal axis. The rotatable coupler 455 can be designed to be oriented perpendicular to the halo member's horizontal rails, e.g., vertically, and parallel to gravity. This orientation can be ensured with a half-dowel design that passed through a semi-circular hole in the AP positioner block 465. The overhead bar 460 can transverse the space between the first 115 and second 120 actuators superior to the patient's head and join the force outputs of the first 115 and second 120 actuators. The overhead bar 460 can be intended to be positioned horizontally to minimize any moment about the patient's halo member 450, e.g., parallel to the horizontal rail and perpendicular to the rotatable coupler 455. The ML positioner block 490 can rigidly attach to both the rotatable coupler 455 and overhead bar 460, using the same semi-circular geometry to maintain proper alignment.

Though only the first actuator 115 has been discussed herein, in some embodiments, the HIT system can comprise two or more actuators. For example, as shown in FIG. 1A, the first actuator 115 can be coupled to a first side of the halo member 450, and the system can further comprise a second actuator 120 coupled to a second side of the halo member 450 and configured to generate an expansion force between the first 105 and second 110 supports. Though not shown, in other embodiments, three or more actuators can be employed and positioned at varying positions to generate the expansion force. Each of the actuators can have any of the features discussed herein as related to the first actuator 115. Purposefully setting the two first 115 and second 120 actuators on different force output settings can allow the clinician to impart controlled moments of torque about the patient's halo and adjust the direction of the traction profile. This may be advantageous in clinical scenarios where the cervical region of the spine cannot properly correct with a completely superior traction profile.

EXAMPLES

The discussion below provides certain examples and methods of operation. This section is for purposes of explanation only and should not be construed to limit the scope of the claims submitted herewith.

A HIT device in accordance with some embodiments of the present disclosure was built and tested. The HIT device comprised two expansion actuators with internal springs on each side of the patient's head. The internal compression spring was chosen to give clinicians approximately 1.0 lbf resolution in force output, analogous to that of HGT, and accommodate the target patient population. The force output of the actuator was controlled by the central adjustment knob and indicated by a metric scale with a scale indicator, shown in FIGS. 1A-B. An internal thread extends up from the actuator, which centralizes the adjustment knob, indicator scale, and compression spring. The knob rotates freely within the actuator, while all other components are fixed. Using embedded spring-loaded plungers, the knob clicks and locks into position at every ⅓ turn, equivalent to a delta of approximately 0.5 lbf in force output. Thus, with two devices fitted in parallel, each ⅓ turn, or "click" is equivalent to a change of approximately 1.0 lbf. In addition, this knob is fitted with an anti-tampering screw that prevents adjustment unless qualified personnel releases it during clinic visits. The top and bottom of each device are fitted in their respective positions with set screws. These methods limit the force output adjustment and the removal of the device to qualified personnel only and maintain the current clinical vernacular used when operating similar orthopedic devices.

The HIT device mounting components secure the anterior-posterior (AP), medial-lateral (ML), and superior-inferior (SI) positions of the devices and allow for the combined force of the two actuators to be translated to the patient's spine. These components are designed with adjustable positioning so the HIT devices can be positioned according to the attending clinician's discretion. Once aligned, the AP and ML position of the HIT device was secured with the hardware and set screws incorporated into the mounting components, while the SI position was set by the TLSO uprights.

Due to the serious risk associated with spinal curvature correction, the HIT device was thoroughly characterized on the benchtop. Prototype devices were tested individually and in parallel to determine their force output at each setting and the induced ML or AP torque, if any.

Figure 5A:
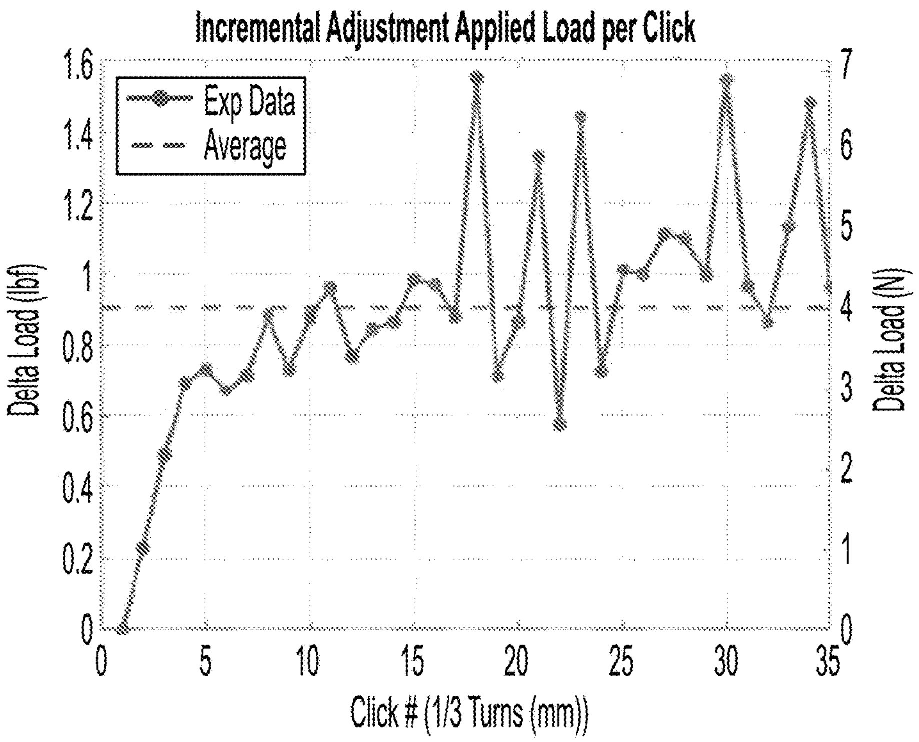
FIGS. 5A-B provide a connected scatter plot (FIG. 5A) showing the change in force output between each consecutive click of two devices in parallel, and a histogram (FIG. 5B) grouping these changes according to their magnitude and prevalence, in accordance with some embodiments of the present disclosure.
Figure 5B:
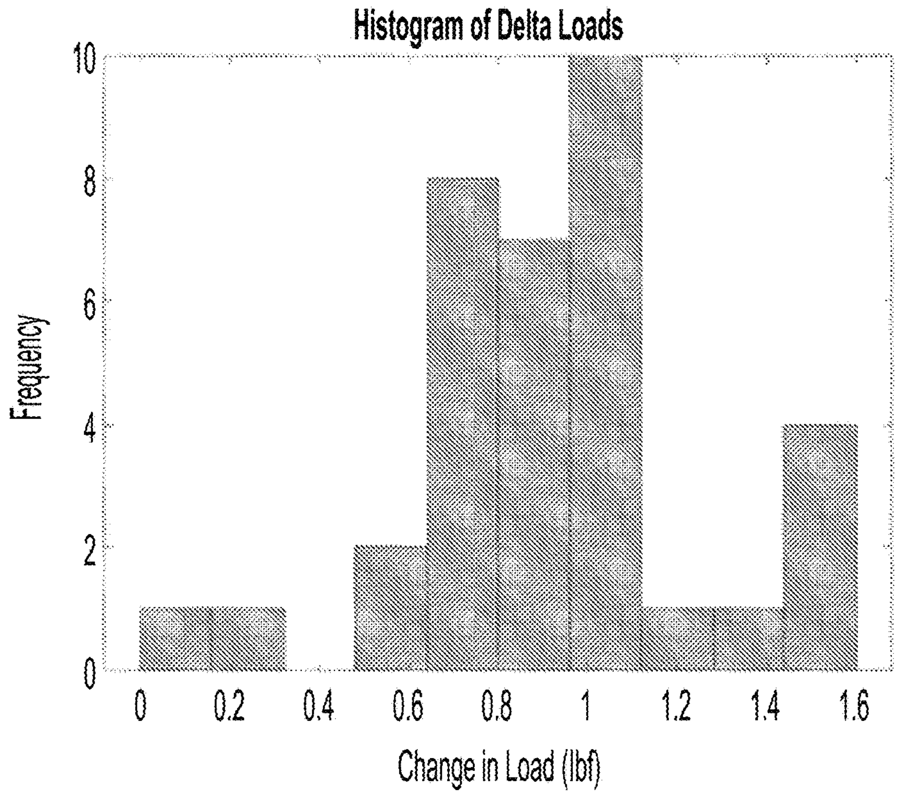

The force output at each setting was measured with an Instron 2530 5kN load cell to determine the precision of the device settings. Two devices were fitted in parallel into the Instron 5965 with a customized testing apparatus that positions the HIT devices in the same manner as the clinical use case, but on the benchtop rather than on a TLSO. The devices were tested in two cases: one in which the force output was increased uniformly throughout the functional range of the devices, beginning at the devices' lower limit, and ending at the devices' upper limit For the other case, the change in force output was determined randomly. In each case, the desired force output was held for 30 s with a sampling rate of 1 ms. This data was averaged and mapped in a connected scatter plot and histogram, as seen in FIGS. 5A-B. This uniform adjustment test results showed a ramp-up period followed by an oscillatory state. The ramp-up period is due to the compression of the testing apparatus itself, rather than directly translating the force to the Instron's load cell for data collection. This problem persists in the later force output settings of the device as the system shows nonuniform changes in force output between adjacent settings. Despite these inconsistencies, the average delta in force output was slightly less than 1.0 lbf at 0.905 lbf, when increased uniformly over the entire range of the device. This error is 9% below the target, but within an acceptable range as seen in the histogram of FIG. 5B, where most of changes in force output are between 0.75 and 1.25 lbf, the bounds of the central bins.

Figure 6A:
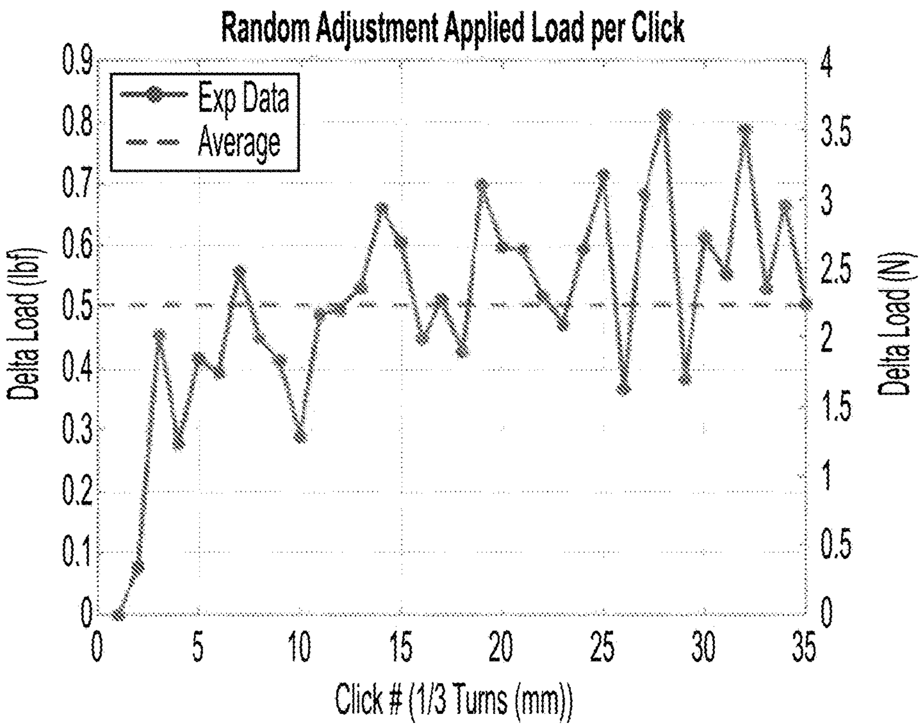
FIGS. 6A-B provide a connected scatter plot (FIG. 6A) showing the change in force output between each adjacent click from a randomized ordering of clicks and a histogram (FIG. 6B) grouping these changes according to their magnitude, in accordance with some embodiments of the present disclosure.
Figure 6B:
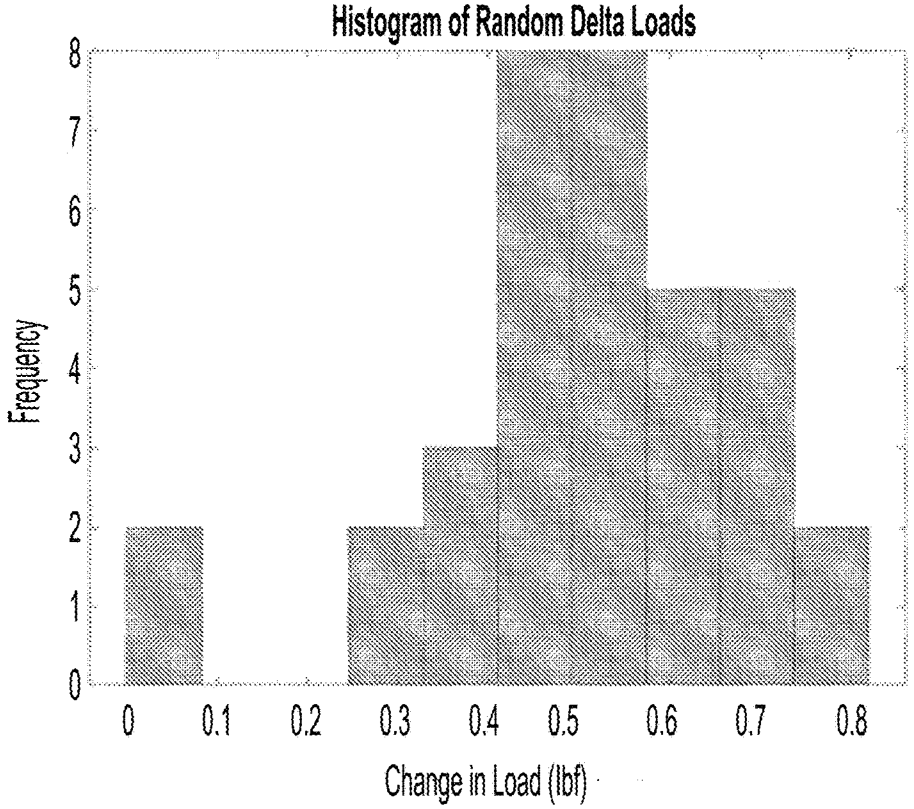

Following this experiment, the process was repeated with a randomized output setting throughout the functional range of the device. This test was necessary to ensure that the proper force output of the device is maintained despite the preceding setting. The results were derandomized and the change between each adjacent force output setting was plotted in FIG. 6A. Again, an initial ramp-up period was seen at the early force output settings of the device. This is consistent with the incremental case and is due to the latency in the testing apparatus. Following this phase, a slight oscillatory behavior about our target force output was seen again. On average, the force output was 1.030 lbf, a 3% error above the target force output. The uniformity of the force output is visualized in the histogram of FIG. 6B with the changes in force between settings appearing normally distributed about the mean.

Figure 7A:
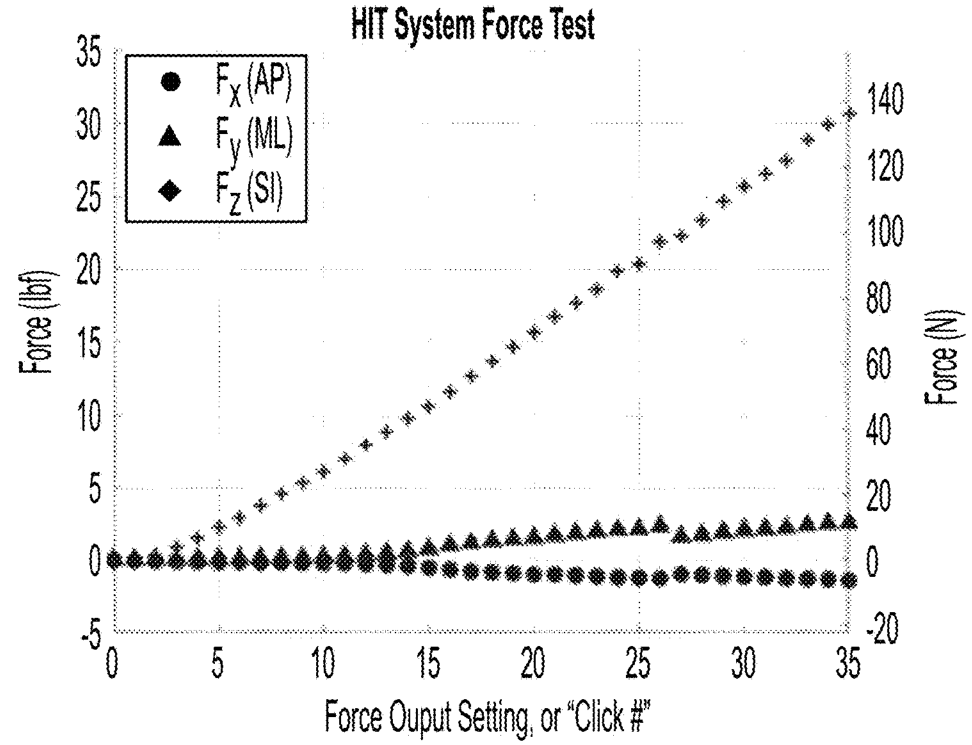
FIGS. 7A-B provide plots of desired force output (FIG. 7A) and minimal ML and AP torque (FIG. 7B) at each setting for an intended use of an exemplary HIT device, in accordance with some embodiments of the present disclosure.
Figure 7B:
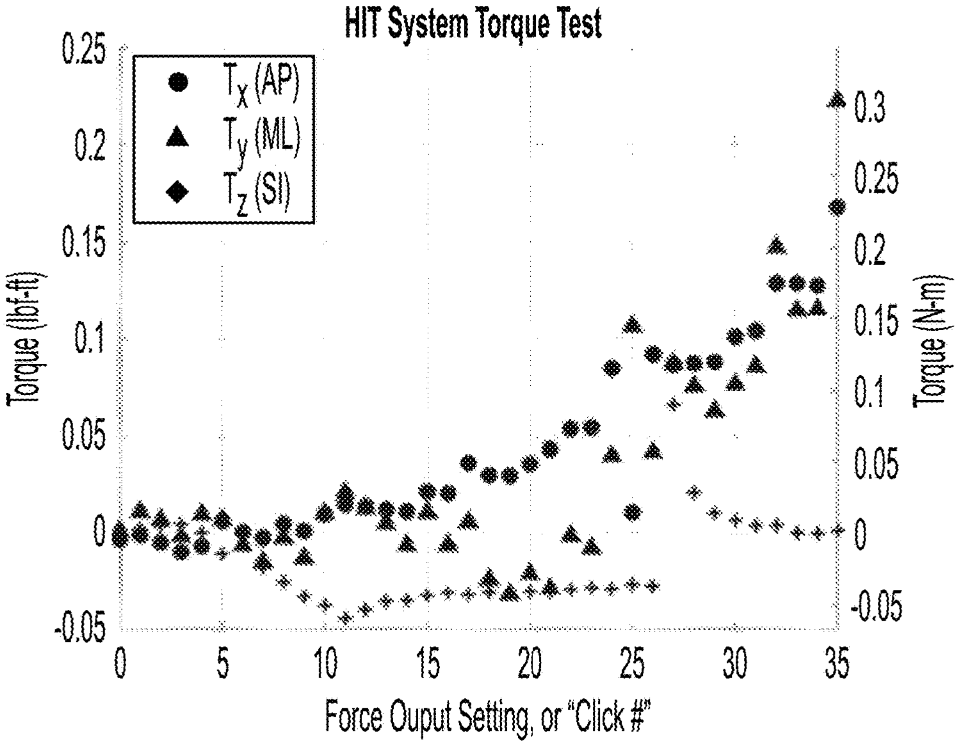

Since two devices are fitted across the patient's halo, an induced torque due to any mechanical difference between the two devices is a major concern. A six-axis ATI mini45 ERA force/torque transducer was used to measure the moment across the sagittal (ML) and coronal (AP) planes. The ATI mini45 was able to collect the force and torque in the AP, ML, and SI directions simultaneously for 5 minutes at a frequency of 100 Hz at each force output setting. The ML torque is the primary concern in this test because the ML force acts on a significantly longer moment atm. The data collected across the 5-minute intervals were averaged and plotted in FIG. 7A to highlight the minimal torque present in the system. As seen in FIG. 7B, the AP (X) torque slightly exceeds 0.15 lbf-ft and the ML (Y) torque slightly exceeds 0.2226 lbf-ft. Both of these torques are within the acceptable safety range as they are less than 0.25 lbf-ft and less than 5% of their force output settings. However, the small amount of torque present increases as the magnitude of the force output of the HIT system increases.

Figure 8A:
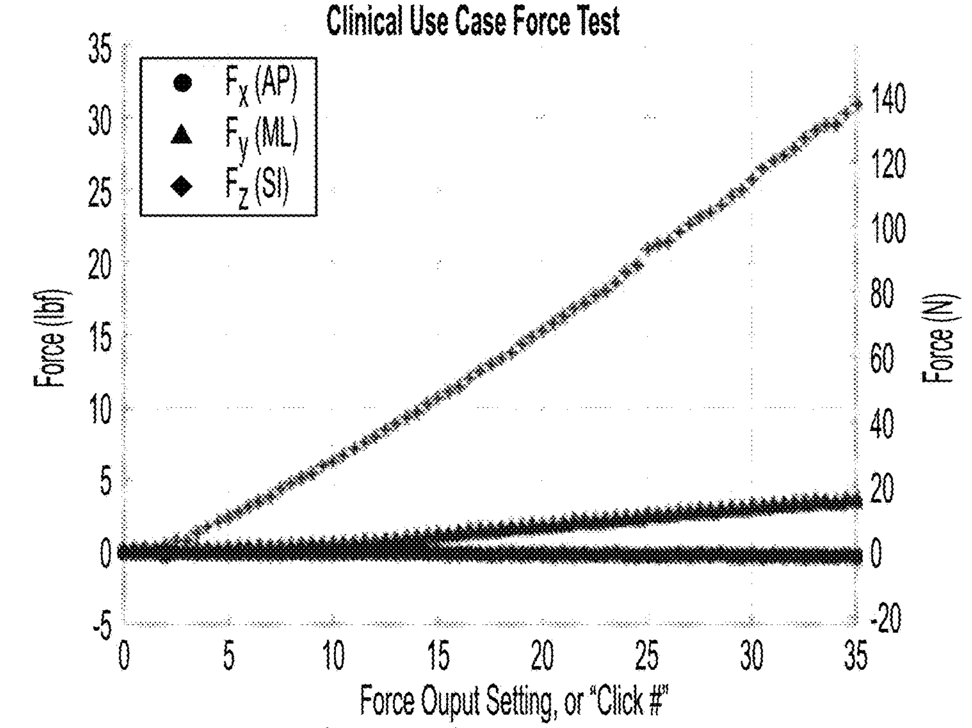
FIGS. 8A-B provide plots of force output (FIG. 8A) and ML and AP torques (FIG. 8B) for each nonuniform and uniform trial representing a clinical use case, which are consistent with the results of an intended use case, in accordance with some embodiments of the present disclosure.
Figure 8B:
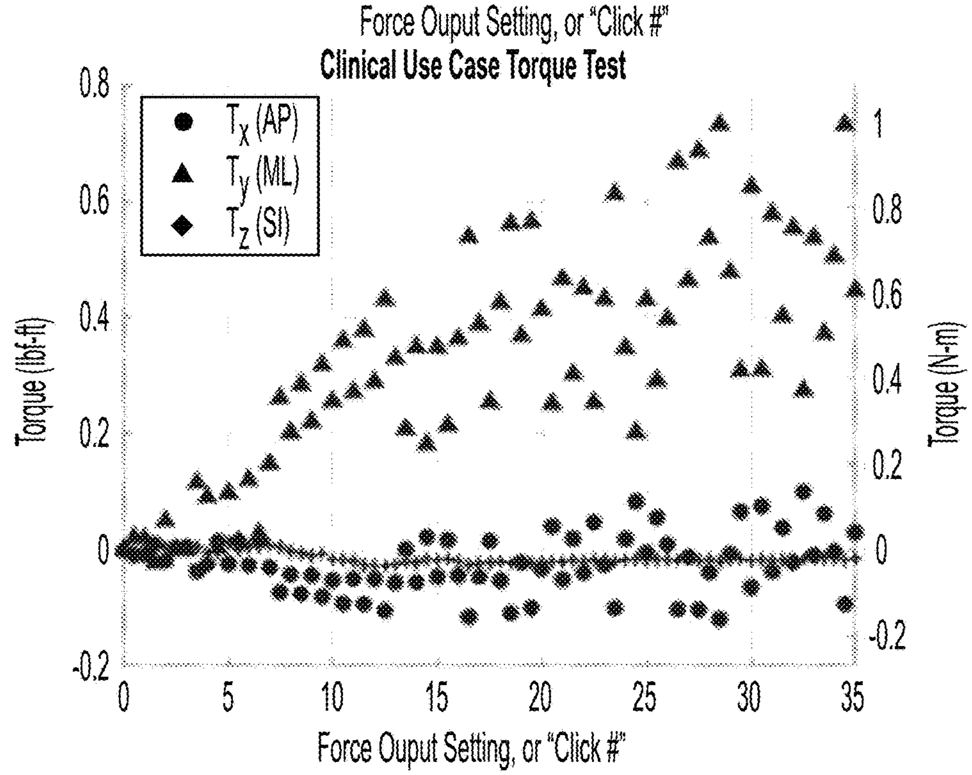

The induced torque during a clinical use case of the HIT system was also investigated. On the benchtop, a clinical scenario in which the force output setting of the bilateral HIT devices briefly differed by ⅓ turns was replicated. This scenario represents the case where a single clinician is adjusting two HIT devices with no assistance. For this experiment, the left or right HIT device was randomly chosen to be set ⅓ turns above the other; this constitutes the nonuniform case. After each non-uniform case, the proper uniform case was established, and data was collected again before moving on to the next nonuniform case. The results represented in FIGS. 8A-B show an increase in ML torque as the force output of the device increases. This is consistent with the results of the initial torque testing. Since the maximum torque was 0.733 lbf-ft at one of the highest torque settings, it is still within an acceptable and safe range at less than 5% of its force output setting. The force output of the HIT system was simultaneously recorded during these tests. As expected, force output linearly and uniformly increased with an increase in click number corresponding to ⅓ turns of the dial. This linear relationship can be seen in FIG. 7A and FIG. 8A for both cases. The upper force output threshold of the HIT system was just over 30 lbf in both cases. Sticking with the clinical standards of HGT, the HIT system can be used for patients weighing no more than 60 lbs. The HIT system can still be implemented on patients weighing more than 60 lbs, but the traditional maximum traction standard would not be met. This may be advantageous depending on the medical scenario and should be assessed by the attending clinician.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

What is claimed is:

1. A halo intrinsic traction system comprising:

a first support configured to attach to a head portion of a patient;

a second support configured to attach to a body portion of a patient, the body portion being below a cervical region of a spine of the patient; and a support connection assembly configured to connect the first support and the second support, the support connection assembly comprising horizontal rails positioned superior the first support;

an overhead bar; and an actuation assembly extending from a lower end to an upper end, the actuation assembly positioned superior to the horizontal rails and configured to:

connect with the overhead bar; and generate an expansion force between the first and second supports;

wherein the overhead bar is configured to transverse a space between the upper end of the actuation assembly.

2. The halo intrinsic traction system of claim 1 further comprising a multi-positioning assembly configured to:

secure an anterior-posterior (AP) position, a medial-lateral (ML) position, and a superior-inferior (SI) position of the halo intrinsic traction system; and allow for the expansion force to be translated to the patient's spine in a desired configuration.

3. The halo intrinsic traction system of claim 2, wherein:

the actuation assembly further comprises a second actuator;

the first support has horizontal rails;

the multi-positioning assembly comprises:

an overhead bar configured to transverse a space between the actuation assembly superior to the first support and join force outputs of the first and second actuators;

rotatable coupler coupling the first support to the actuation assembly, such that rotation of the rotatable coupler alters a direction of the expansion force;

an anterior-posterior (AP) positioning subsystem comprising:

an anterior-posterior positioner block; and an anterior-posterior positioner hardware;

a rail interface; and a bottom mount;

the expansion force is transferred to the first support via the overhead bar and the rotatable coupler; and the AP positioning subsystem and the bottom mount interface with the horizontal rails via the rail interface.

4. The halo intrinsic traction system of claim 3, wherein the rotatable coupler is:

mountable to the first support and rotatable about a frontal axis; and configured to be oriented perpendicular to the horizontal rails.

5. A method of treating scoliosis and/or kyphosis in a patient in need thereof with the halo intrinsic traction system of claim 1, the method comprising:

attaching the first support to the head portion of a patient;

attaching the second support to the body portion of the patient; and generating, with the actuation assembly positioned superior to the horizontal rails and connected to the overhead bar, the expansion force between the first and second supports.

6. The method of claim 5 further comprising adjusting a magnitude of the expansion force.

7. The method of claim 5 further comprising:

anti-tampering locking the actuation assembly between a locked and an unlocked position; and moving the actuation assembly between a plurality of positions only when the actuation assembly is in the unlocked position.

8. The method of claim 5 further comprising at least two different expansion forces with the actuation assembly.

9. The method of claim 5 further comprising altering a direction of the expansion force.

10. The halo intrinsic traction system of claim 1, wherein the first support comprises a halo member configured to attach to the head portion of the patient.

11. The halo intrinsic traction system of claim 10, wherein the halo member is coupled to the actuation assembly via a rotatable coupler, such that rotation of the rotatable coupler alters a direction of the expansion force applied to the first support relative to the second support.

12. The halo intrinsic traction system of claim 1, wherein:

the actuation assembly comprises at least a first actuator; and the first actuator comprises a spring configured to generate the expansion force.

13. A halo intrinsic traction system comprising:

a first support configured to attach to a head portion of a patient;

a second support configured to attach to a body portion of a patient, the body portion being below a cervical region of a spine of the patient;

a support connection assembly configured to physically connect the first and second supports, the support connection assembly comprising horizontal rails;

an overhead bar; and an actuation assembly positioned superior to the horizontal rails and configured to connect to the overhead bar and generate an expansion force between the first and second supports;

wherein:

a location of the actuation assembly is such that the expansion force is transferred to the first support from above the first support;

a location of the second support provides for transfer of the expansion force below the cervical region of the spine; and the actuation assembly comprises a first actuator comprising an adjustment actuator configured to adjust a magnitude of the expansion force between the first and second supports.

14. The halo intrinsic traction system of claim 13, wherein the adjustment actuator is moveable between a plurality of positions, each position corresponding to a different magnitude of the expansion force between the first and second supports.

15. The halo intrinsic traction system of claim 14, wherein:

the actuation assembly further comprises an anti-tampering lock configured to transition between a locked and an unlocked position; and the adjustment actuator is moveable between the plurality of positions only when the anti-tampering lock is in the unlocked position.

16. The halo intrinsic traction system of claim 14, wherein each of the plurality of positions corresponds to a predetermined fixed incremental change in the magnitude of the expansion force between the first and second supports.

17. The halo intrinsic traction system of claim 13, wherein:

the actuation assembly further comprises one or more other actuators; and the first actuator and one or more of the other actuators are configured to generate differing expansion forces.

18. The halo intrinsic traction system of claim 13, wherein:

the first support comprises a halo member configured to attach to the head portion of the patient;

the support connection assembly further comprises rods with direct contact with the horizontal rails and without direct contact with the actuation assembly;

the actuation assembly further comprises a second actuator;

the first actuator is coupled to a first side of the halo member; and the second actuator is coupled to a second side of the halo member.

* * * * *